United States Patent
Tweedie et al.

(10) Patent No.: US 6,902,897 B2
(45) Date of Patent: Jun. 7, 2005

(54) BIOCHIP DEPOSITION SYSTEM AND METHOD

(75) Inventors: Mark Tweedie, Co. Antrim (GB); John Victor Lamont, Co. Antrim (GB); Robert Ivan McConnell, Co. Antrim (GB); Stephen Peter Fitzgerald, Co. Antrim (GB)

(73) Assignee: Randox Laboratories, Ltd., Crumlin (GB)

( * ) Notice: Subject to any disclaimer, the term of this patent is extended or adjusted under 35 U.S.C. 154(b) by 261 days.

(21) Appl. No.: 10/188,796

(22) Filed: Jul. 5, 2002

(65) Prior Publication Data

US 2003/0008385 A1 Jan. 9, 2003

(30) Foreign Application Priority Data

Jul. 6, 2001 (GB) ............................................. 0116575

(51) Int. Cl.⁷ ........................... C12Q 1/68; C07H 21/02
(52) U.S. Cl. ........................ 435/6; 435/91.2; 536/23.1; 536/24.3
(58) Field of Search ................... 435/6, 91.2; 536/23.1, 536/24.3

(56) References Cited

U.S. PATENT DOCUMENTS

| 6,232,072 | B1 |   | 5/2001 | Fisher |   |
|---|---|---|---|---|---|
| 6,263,292 | B1 | * | 7/2001 | Fiekowsky | 702/95 |
| 6,558,623 | B1 | * | 5/2003 | Ganz et al. | 422/63 |
| 6,642,054 | B2 | * | 11/2003 | Schermer et al. | 436/43 |

FOREIGN PATENT DOCUMENTS

| GB |   | 2 355 716 A | 5/2001 |
| WO | WO | 99/49346 | 9/1999 |
| WO | WO | 01/62377 | 8/2001 |
| WO | WO | 02/04123 | 1/2002 |

* cited by examiner

*Primary Examiner*—Jeffrey Fredman
(74) *Attorney, Agent, or Firm*—Oliff & Berridge, PLC

(57) ABSTRACT

A biochip deposition system and method. The system comprises a deposit mechanism for depositing organic material in spots on a substrate; and a viewing system for detecting the spots on the substrate during a deposit operation and before the spots have dried, for determining if the spots have been correctly deposited, and if not, for generating a suitable output signal. The viewing system includes an illumination device for illuminating deposited spots at a relatively low angle relative to the substrate.

23 Claims, 10 Drawing Sheets

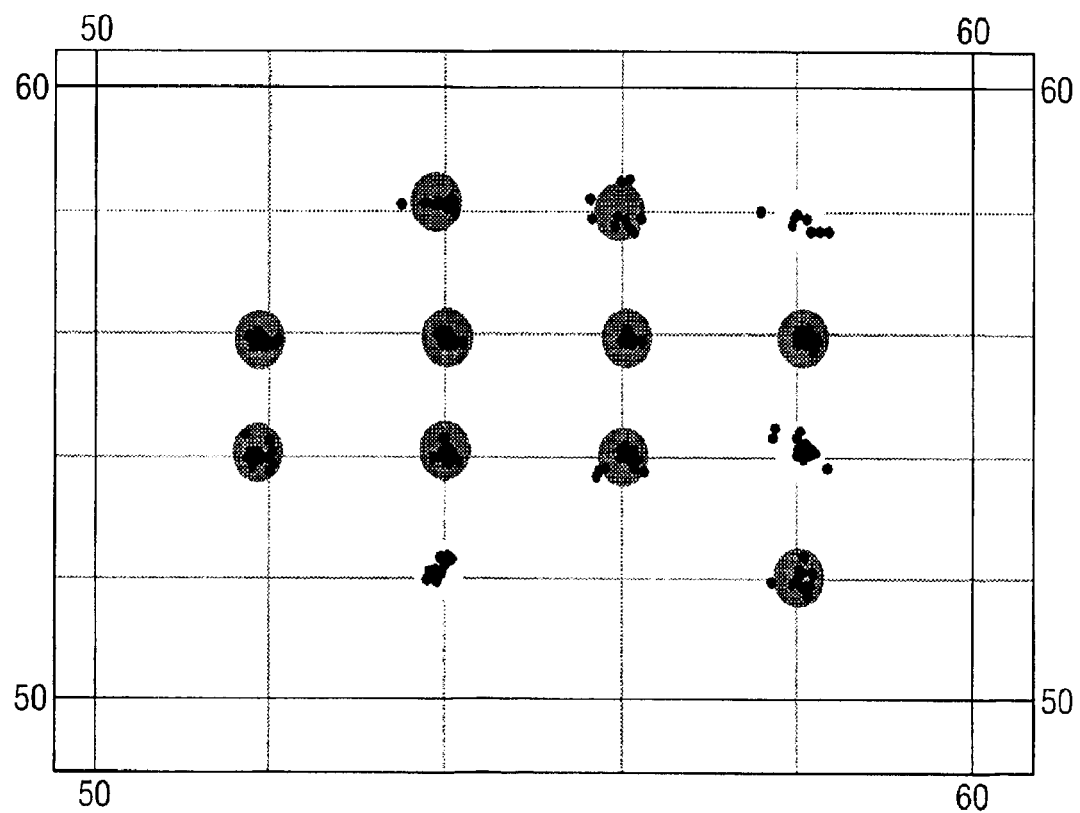

BIOCHIP DEPOSITION SYSTEM AND METHOD

The present invention relates to a biochip deposition system and a method of monitoring a biochip deposit process, by for example measuring the relative positions of arrays of spots of organic material deposited on suitable substrates, forming biochips.

Clinical analytical equipment (or analysers), for performing biological assays for clinical diagnostics, often use measurements of biochemical reactions on the surface of a prepared biochip substrate, having a predefined array of discrete reaction sites thereon. The array of e.g. antibodies (or proteins, or other biological molecules) is, typically, prepared by deposition from proprietary liquid dispensing equipment, as discrete spots, onto an array of substrates, which may, ultimately be further separated, after such preparation, into individual biochips, for storage prior to future use in the aforementioned analysers In known equipment, the effect of the tip of a dispenser on the form of a spot is tested by causing the dispenser to dispense a liquid drop at a testing station while it is viewed. The form of the drop can be monitored on a display or the like. However, it has been found that this test is insufficient to overcome a number of errors which can occur with such spotting equipment which can render biochips outside the specification required for use in the intended analyser—such chips need to be screened out so that they are not used in the intended analyser, as they could, potentially, give false results. Typical errors are spots missing due to dispense failure, spots misplaced due to variable air currents and electrostatic forces (for an insulating substrate), spots misplaced due to stepper motors losing step counts on the moving arms (possibly from accidental impact), satellite spots formed by break-up of the spot at the tip of the dispense head, and dispense heads jetting, forming large streaks, instead of discrete spots, on the substrate.

Spots missing can lead, in certain assay types, where the signal output is inversely proportional to the amount of analyte being tested for, to a false diagnosis of a strong positive sample, which is a very undesirable situation in the diagnosis of diseases, etc. Misplaced spots can lead to misdiagnosis, as the spots may be mistaken for adjacent spots (which are often for a different test) in the analyser, or, if sufficiently misplaced, may not be found, again, leading to a false positive. Satellites can fall on or near other spots, leading to cross-talk between the different test regions, and, therefore false results. Clearly, some error trapping is used in such analysers, but it is desirable to minimise the risk of such faulty chips passing the quality control process, in the first instance.

Note that the only one of the above errors which can be detected by the deposition equipment, itself, is the dispense failure, since this can be found from the pressure changes in drop dispense, if the heads have been fitted with pressure sensors—often, however, this condition is not sounded as an alarm to the operator, since the equipment just counts the total number of spots dispensed, as a basic spot number confirmation, available at the end of a spotting run, which may take several hours.

Quality control testing on such biochips, using a small sample, is feasible, and involves e.g. taking 1–3 biochips from each substrate, running these through the analyser, and examining them for gross defects. However, this is always a post-deposition quality control process. An example of a known deposit process monitoring system is described in GB-A-2355716 which relies on the presence of dried salts to give a measurable image of droplet position. The problem with this approach is that it relies on the presence of salts in the deposited droplets.

U.S. Pat. No. 6,232,072 describes a system for overcoming the problem that it is difficult to obtain sufficient reflected light from the droplets or substrate surface. Their solution is to use a transparent substrate with a mirror underneath. Light shines through from the front of the substrate and is reflect off the mirror to be imaged by a camera. Clearly, this solution is not suitable for use with opaque and translucent substrates.

In accordance with a first aspect of the present invention, a biochip deposition system comprises a deposit mechanism for depositing organic material in spots on a substrate; and a viewing system for detecting the spots on the substrate during a deposit operation and before the spots have dried, for determining if the spots have been correctly deposited, and if not, for generating a suitable output signal, wherein the viewing system includes an illumination device for illuminating deposited spots at a relatively low angle relative to the substrate.

In accordance with a second aspect of the present invention, a method of monitoring a biochip deposit process comprises a) detecting spots of organic material as they are deposited on a substrate and before the spots have dried, the detecting step including illuminating the substrate at a relatively low angle;

b) determining if the spots have been correctly deposited; and, c) if not, generating a suitable output signal.

In contrast to the known systems, we provide a system which can monitor the spots as they are deposited. In many cases, once a spot has dried, it is very difficult to detect but by viewing the spots before they have dried by using low angle illumination, it is possible to detect and view them under reflection and thus on opaque and translucent substrates. In this context, low angle illumination means either dark-field or grazing incidence illumination, i.e. near parallel to the plane of the surface, and would typically be nominally, in the range, 0° to +2°, preferably 0 to 1° from parallel. The effect of this is to highlight surface texture and imperfections, specifically, in this case, the freshly deposited droplets which show up as bright against a darker background.

The system can perform, at least, basic presence/absence analysis, during deposition, and sound an alarm, if deposition fails, for some reason. This, then, allows the deposition to be stopped, the equipment examined, the fault diagnosed and corrected, and the deposition re-started with the minimum of faulty chips being produced. The possibility also exists to extend this to full positional analysis, in real-time, rather than by post-deposition analysis. In other words, steps (b) and (c) could be carried out after completion of the deposit process or during the deposit process.

The viewing system typically comprises a camera such as a, preferably two-dimensional, CCD array although other viewing systems could also be used. An advantage of the invention is that the camera viewing angle can be set at any position that suits the deposition system construction, i e. it is not at a complementary angle to the light source angle, in contrast to U.S. Pat. No. 6,232,072.

The spot analysis (either by post-deposition processing, or real-time processing) of the machine vision system data per substrate, allows a record to be produced of spot coordinates per biochip, as well as an output of faulty chip coordinates. The latter coordinates would, typically, be passed in a data file to a separate reject chip marking station, which may mark the rejects with a clearly detectable material which shows a detectable colour, light level or densitometric change such as a coloured dye, ink or wax, so that they may, subsequently, be removed from the biochip production run, by a pick and place machine, and, thus, cannot be used later in the analyser, by mistake. The record, itself, forms a useful quality assurance tool, providing traceability of the biochip production, in the event that queries about production standards on particular chips are returned from laboratories using the analysers—as implied, this degree of traceability (particularly on spot position) is not available when using the deposition equipment alone.

Typically, the detecting step comprises locating the spots; detecting a first pair of edges of the substrate; detecting the position of the located spots relative to the substrate edges; and determining if each spot is located at an expected position relative to the substrate edges. The spots should be located with respect to at least 2 orthogonal substrate edges, and, preferably, with respect to 2 near-parallel opposite edges (one of which is likely to be one of the 2 orthogonal edges) in order to correct perspective distortion This leads to a further advantage since the method can be used where the entire pattern is not visible at once, but is built up in multiple depositions, over multiple substrates. The post-deposition analysis can allow the superposition of the multiple-deposition-sequence spot positional data, so as to reconstruct the entire pattern afterwards, for each of the substrates in turn.

An example of a system and method according to the present invention will now be described with reference to the accompanying drawings, in which:

FIGS. 9a and 9b illustrate various screen displays;

The basics of the machine vision system of the preferred example consist of a camera (with either analogue or digital video output) viewing the substrates to be spotted, and interfaced to a suitable framegrabber in a PC, on which is running the machine vision program. The program operates on selected frames to examine the substrates to find the coordinates of the deposited spots with respect to the edges of each substrate. These coordinates are output to a file for record purposes, and to another program module for real-time monitoring, the most basic implementation being for presence/absence determination. Post-deposition processing for more detailed spot positional analysis is utilised in a first implementation, and can be extended to real-time processing in a similar manner. The output of the camera may be further archived to analogue or digital videotape, or hard disk, as appropriate.

Figure 1A:
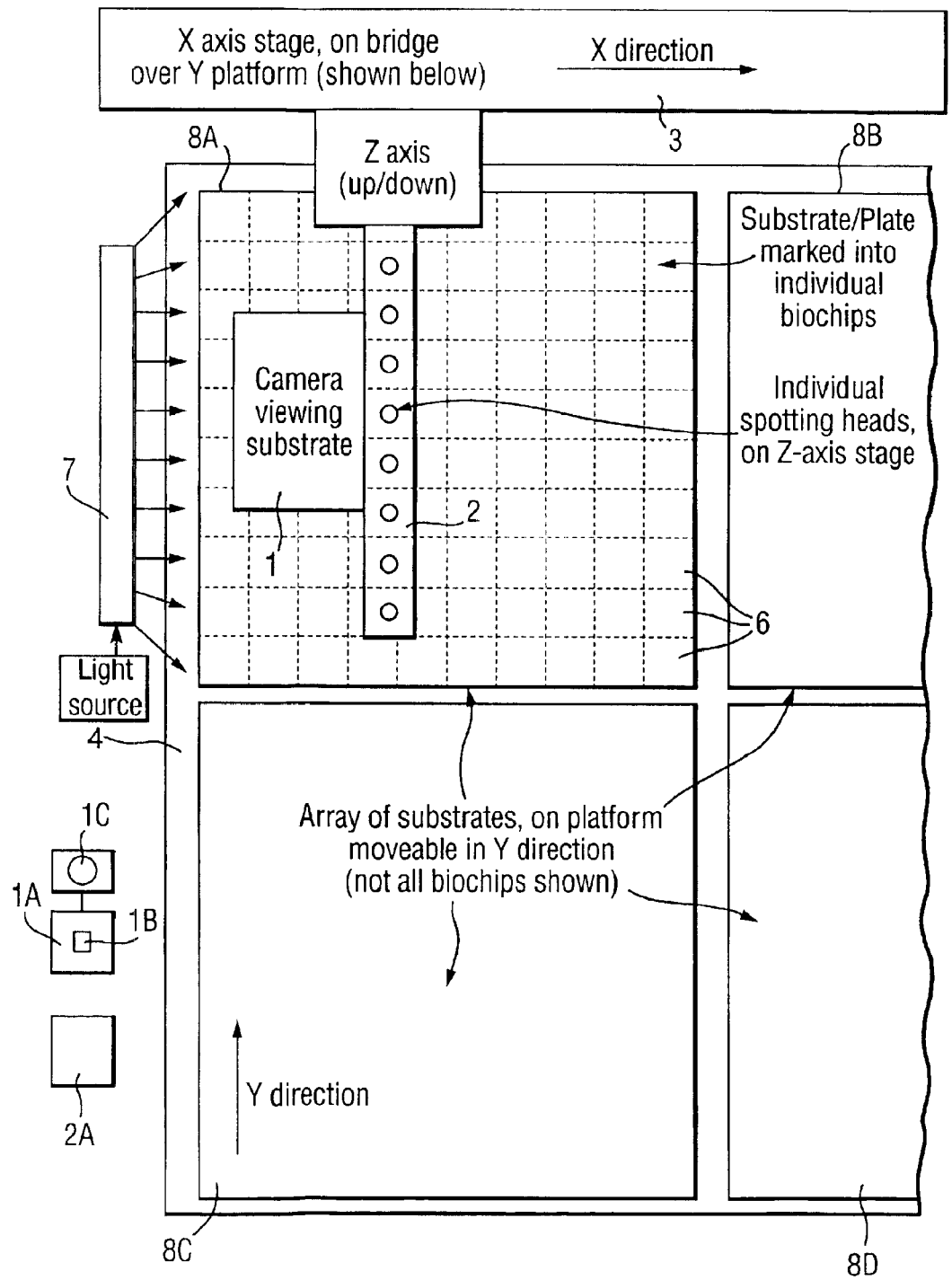
FIG. 1A is a schematic (truncated) plan view of the system.

A schematic diagram of a typical multi-dispense head spotter, is shown in FIG. 1A, where a camera 1 is mounted to the left hand side of multi-dispense head 2, viewing, downwards. The camera 1 is connected to a framegrabber and image processing system 1A, including a processor 1B and a monitor 1C while the multi-dispense head is controlled in a conventional manner by a controller 2A. In this implementation, the multi-dispense head 2 is fixed to a bridge 3, with stepper motors (not shown) allowing movement in the X direction shown, whereas a substrate bed 4 moves under the multi-dispense head 2 in the Y direction. If the Y axis is held stationary, and deposition starts on the left hand side, then the camera 1 will see each fresh set of spots as they emerge from under the dispense heads, as they are indexed in the X direction. Other scan arrangements are possible, by changing the camera viewpoint, accordingly. FIG. 1A shows four substrates or plates 8A–8D located on the base 4.

In a preferred embodiment, the spacings of the multi-head dispensers are matched to the spacings of individual biochips (only some indicated in FIG. 1A by reference 6)—this allows all biochips on all substrates on the bed to have one spot of one antibody (or other organic material) deposited. The heads can be cleaned, and the second antibody type can be deposited on all biochips, in a different location, pre-defined in the deposition array program, controlling the spotter X-Y position.

Figure 1B:
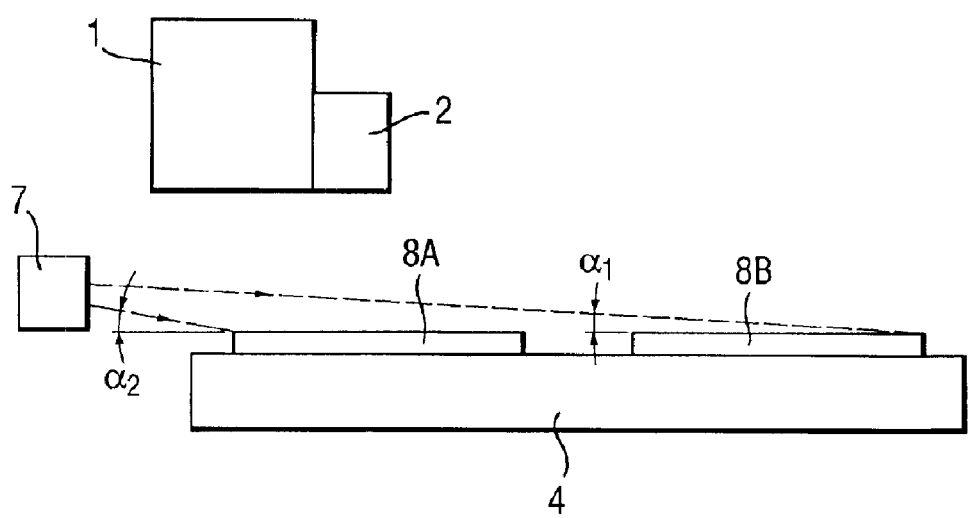
FIG. 1B is a schematic cross-section through part of FIG. 1A.

A light source 7, such as a continuous, fibre optic white light, is also shown to the left hand side of the spotter 2, and, in such an application, would be set to give very low angle incidence with respect to the substrates so as to achieve dark field illumination. This angle ($\alpha1, \alpha2$) is typically in the range 0–2° to the plane of the substrate as shown in FIG. 1B. The reason for low angle illumination is because such droplets are, often, in the range of a few nanolitres to a few tens of nanoliters, and, hence, around 0.2 to 0.7 mm in diameter, so grazing incidence is required to highlight them, when on a diffuse, opaque substrate. The image to be processed usually consists of small bright spots, highlighted against the substrate background. The spot contrast with the background varies due to spot size, variability in lighting conditions, video noise in the camera output signal, and because the spots are in the process of drying while being measured.

The image processing system 1A extracts frames at regular intervals (e.g. 0.5 seconds) from the framegrabber. For each frame, the processor 1B within the system 1A analyses the image as now described with reference to FIGS. 2 to 8.

Figure 2:
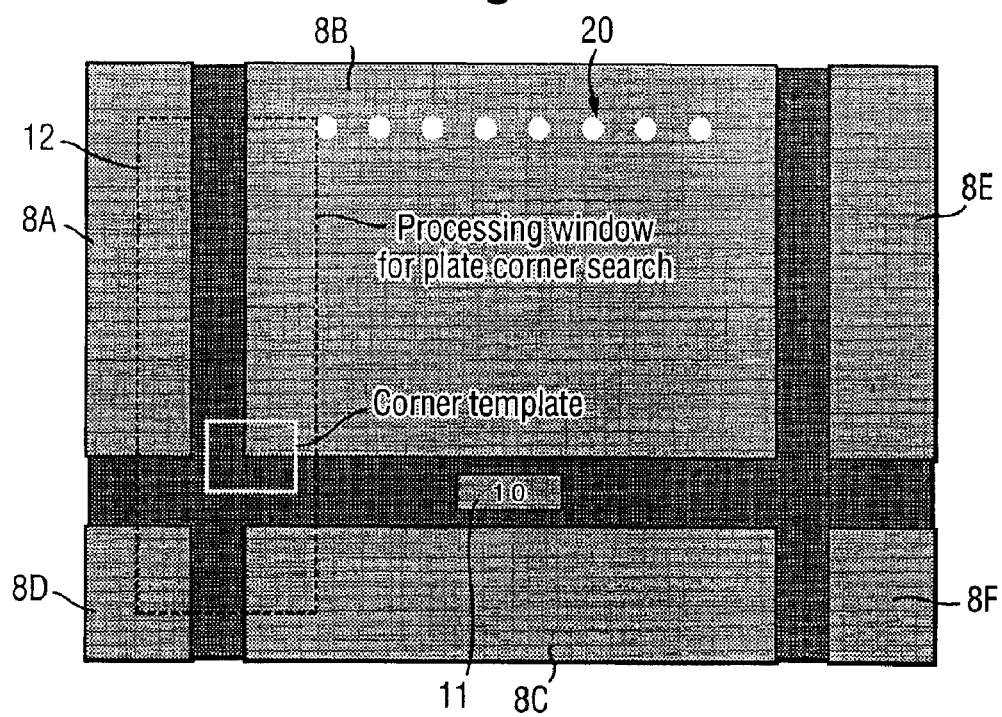
FIG. 2 is a typical camera field of view of a substrate illustrating a search window.

A typical field of view to be processed, in this preferred embodiment, is shown in FIG. 2, where the substrates 8A–8D (and 8E, 8F) are shown fixed in different locations in the bed 4. Each location is designated with a number, character sequence, or standard barcode 11, readable by standard machine vision optical character recognition and bar code reading software. The purpose of these markings is to uniquely identify which substrate is being examined for spot data. In this example, the plates 8A–8F move from top to bottom of the image while being spotted.

Figure 3:
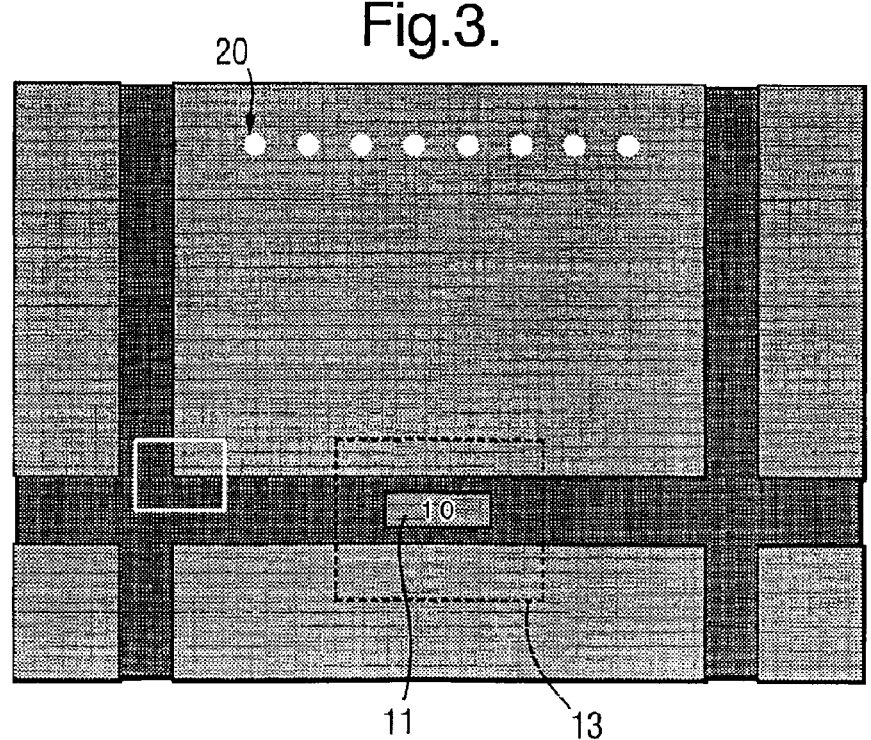
FIG. 3 is a view similar to FIG. 2 but illustrating a search window for ID characters.
Figure 4A:
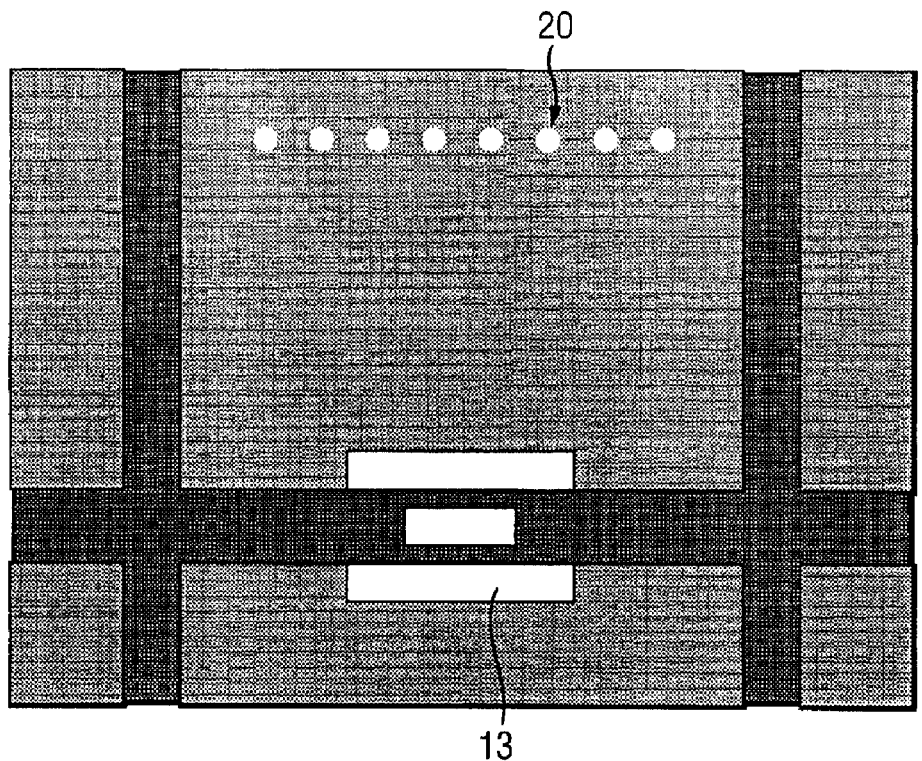
FIGS. 4a and 4b are views similar to FIG. 2 showing determination of the ID characters.
Figure 4B:
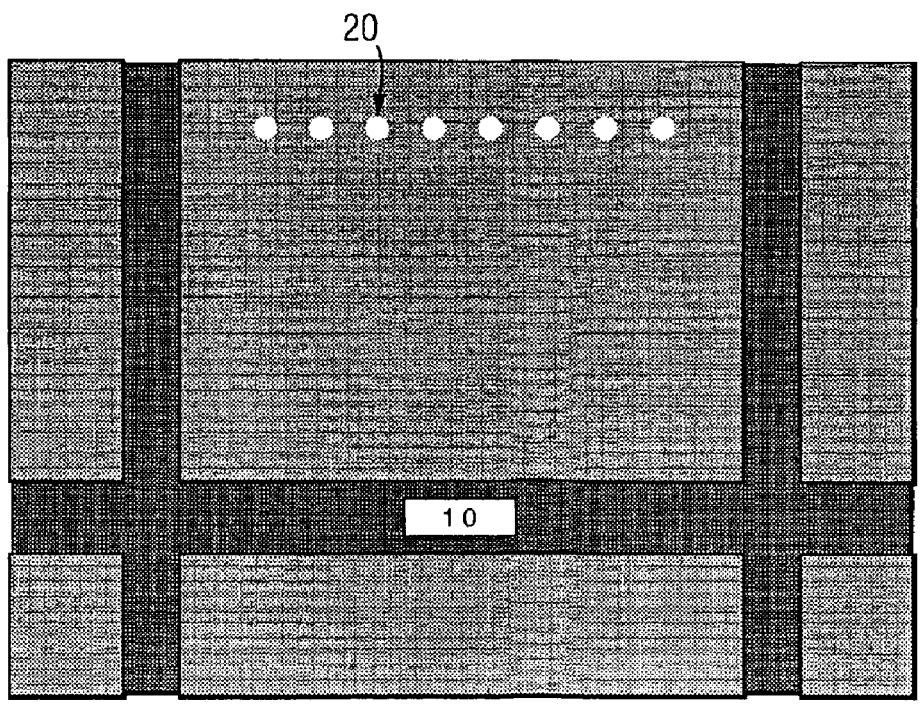

A search window 12 is used to search for the bottom edge or one corner of the substrate, by template matching—the diagram in FIG. 3 shows a corner search. The location of the corner (or the bottom edge) is then used to key a window 13 to find and read the substrate identification markings 11—this means that as the substrate traverses the image, the substrate ID window tracks the movement of the bottom corner or edge of the substrate, so that it examines the correct area, Segmentation, a standard image processing technique for separating image regions according to a threshold, is used to find and highlight the light areas in the substrate ID window 13, as in FIG. 4a, and then further segment these into dark areas (assuming dark characters on a light background) to find the letters/numerals/barcode, according to a pre-determined threshold, as in FIG. 4b. The segmented dark areas, recognised as separate objects, are then examined, in this example, by an optical character recognition routine, thus giving the substrate ID number—a typical implementation of this would use a neural network classifier, trained on a set of sample characters, to provide robust character recognition, that is less sensitive to character size variation than template matching. NeuroCheck® is a good example of a commercially available machine vision program, from DS GmbH, that includes neural network classifiers, image segmentation, and the various other features required to perform all the standard recognition, spot-finding, and distance gauging tasks described herein.

Figure 5:
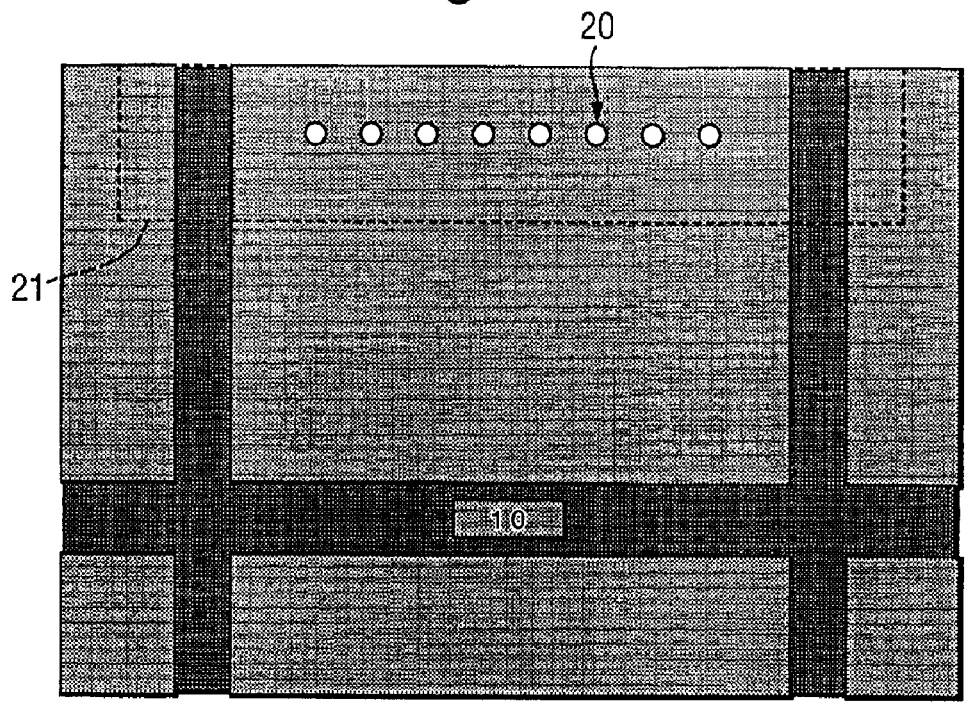
FIGS. 5 to 8 are views similar to FIG. 2 showing the location of spots.
Figure 6:
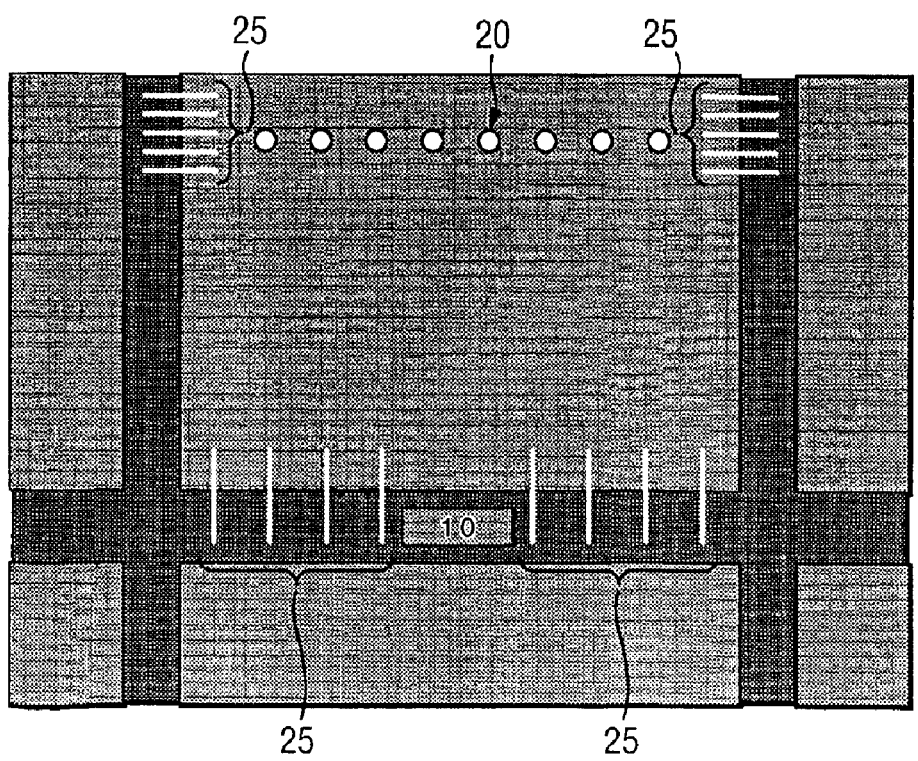

Having identified the substrate, the next task is to find the spots 20—in this example, a fixed window 21, just below the top of the image may be used, over which a suitable filter (e.g. A Top Hat filter, which is specifically for spot-finding) may be run to find the spots, as in FIG. 5 (the found spots are outlined in black). An alternative method could be to copy the image window, heavily smooth the copy, and subtract it from the original, although this is more susceptible to noise in non-uniform lighting situations. The filtered images would then be thresholded, to reject small noise artefacts, and a function such as blob analysis (or "Create regions of interest by thresholding", in NeuroCheck) used to separate individual spots for feature measurement—blob analysis uses the standard Freeman chain code (see Industrial Image Processing, Demant, Streicher-Abel and Waszkewitz, Springer 1999, pp 104 to 108) to follow the outer contour of each segmented spot, and, thereby, identify the pixels included within the spot. The features of each spot can then be calculated (e.g. spot (x,y) coordinates, area, contrast, aspect ratio, etc.) and limits set on these to screen spots for acceptability, and, thereby reduce false detections, and noise pick-up in the positional measurements.

Figure 7:
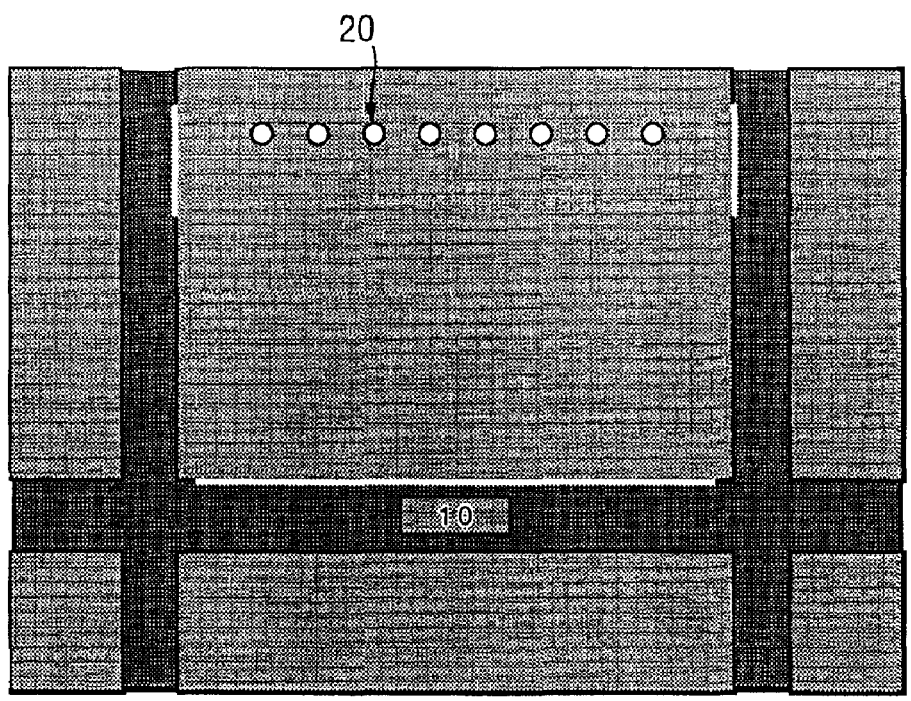

The next stage is to measure the spot locations with respect to the substrate edges, to provide a set of on-substrate coordinates. To find an edge over an extended region, a typical technique is to use a set of edge-crossing polylines 25, for each of which the gradient of the light level profile is examined to find the centre of the slope—a model line can be computed from several edge crossings to provide the equation of a line fitted to the edge in question. Here, a set of polylines would be used, as in FIG. 6, on both left and right hand sides of the substrate, and a set on the bottom edge, keyed in the Y direction, from the position of the substrate, found by the corner template match. Naturally, in this example, the lines on the left hand side would be searched for a rising edge, those on the right hand side for a falling edge, and those on the bottom edge, for a falling edge, also. The model lines, fitted to the found edges, are shown in FIG. 7.

The purpose of measuring from both left and right hand sides is to decrease any errors due to perspective distortion, which occurs when the camera is not exactly vertical to the substrate—the distance between left and right edges is known in real world coordinates, so any image size variations are accounted for in, at least the X axis. The same cannot be done in the Y axis, since the top of the plate is mostly obscured by the spotting heads, and the greater number of spots would be dried out before the substrate fully exits from under the multi-dispense heads.

Figure 8:
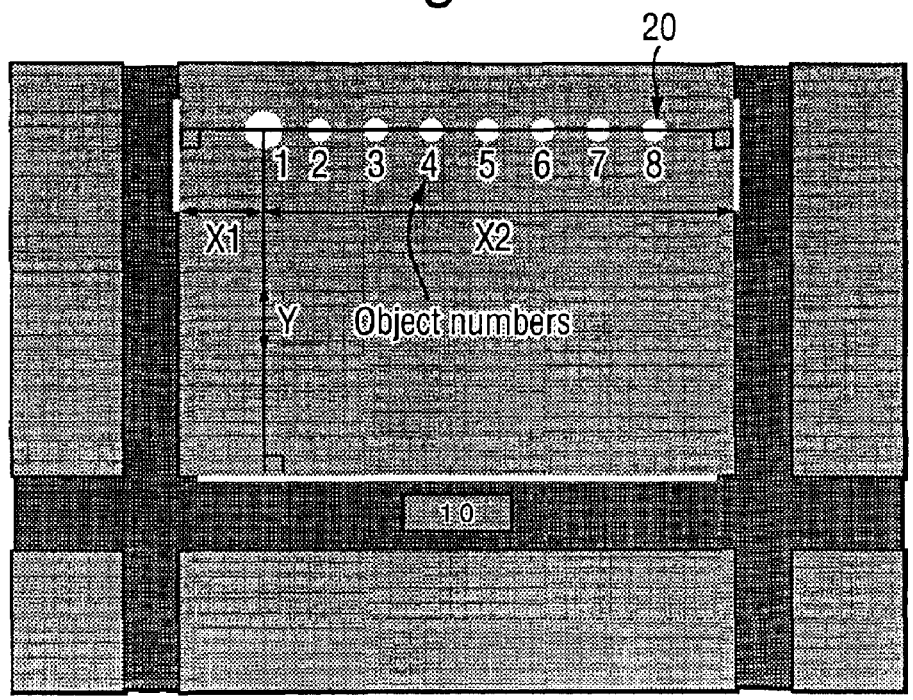

The edge-fitted lines, calculated above, are then combined with the spot data, and the result allows gauging (distance measurement) functions to be used. The gauging function allows a designated point object to be measured with respect to, in this case, each of the 3 different line objects calculated for the substrate edge fits. An example of distance gauging is shown in FIG. 8. The machine vision program is written to gauge all spots detected within the processing window, up to a pre-defined maximum, and to output the results to a designated data file—a typical data file would be in the form of a standard csv file, so that one line will have the detected substrate number, and the next line will have the gauged spot coordinates, and so on. Hence, for post-deposition positional processing, there will exist a data file containing an interleaved list of substrate numbers and associated data points for the detected spots. This data file has to be read by a suitable analysis program so that the spot position detections are assigned to the correct substrate, but this is just a matter of reading the substrate number first, and taking the data from the following line to be assigned to that substrate.

For real-time spot presence verification, it is obvious that the gauged spot positions must be analysed at once—this can be achieved, in this example for NeuroCheck programs, by using a user-defined function that plugs into the main program (using NeuroCheck's plug-in DLL (dynamic linked library) capability). The plug-in function could be used to count the number of spots detected per biochip. The number of spots detected could be averaged over several camera frame samples, because video noise can result in some spots not being detected in one frame, but clearly detectable in the next frame. Additionally, the spots often contain buffer salts, which can be visible after drying, so that these can sometimes be detected as well as the fresh spots, possibly, rendering a simple spot count unreliable. Also, the spots appear to oscillate slightly in position, due to video noise and timing jitter, so an average position must be calculated.

Figure 9A:
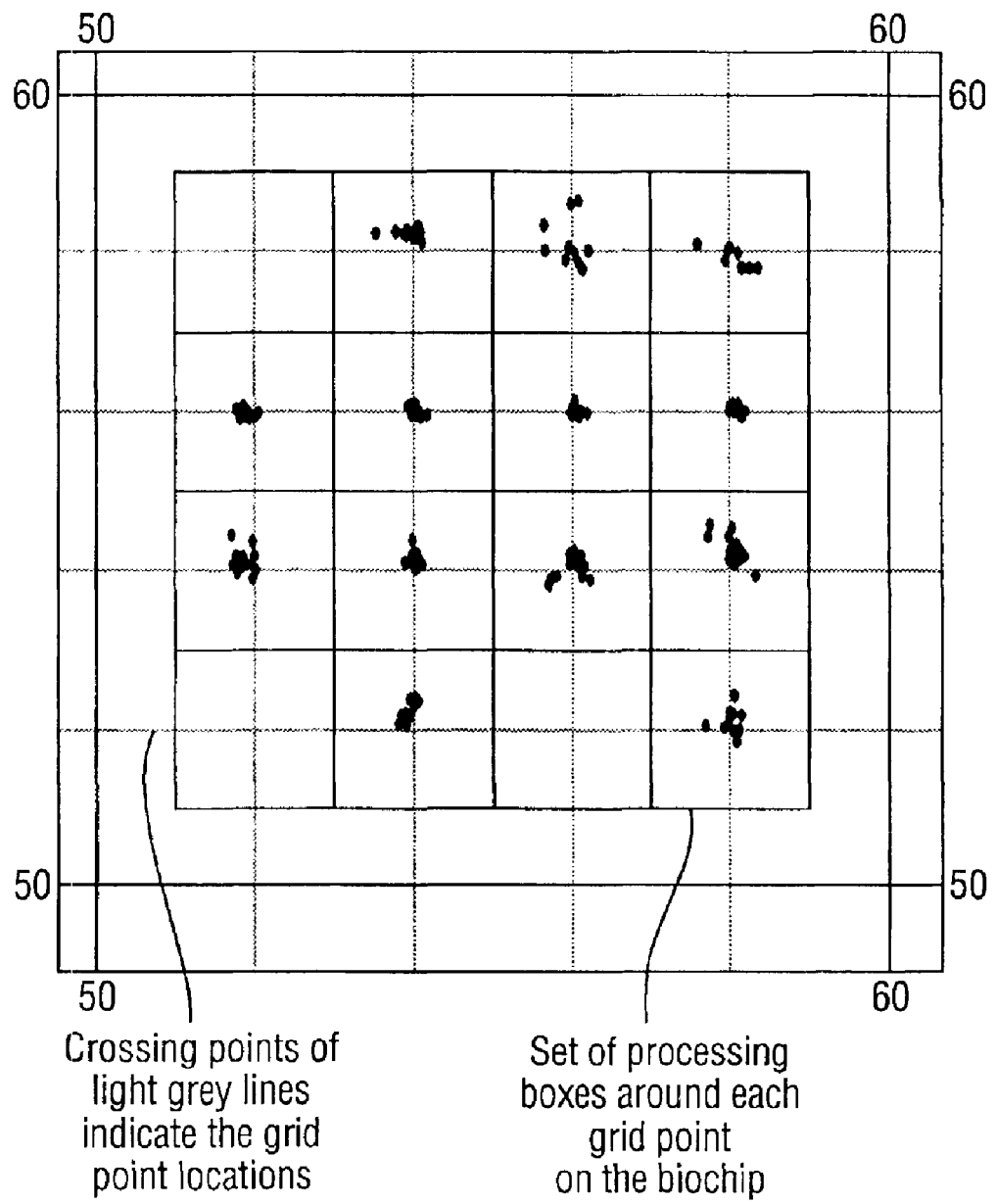

For the above reasons, it is usually necessary to assign a set of processing windows per biochip, on a grid that matches their intended positions, as in FIG. 9a. Within each window, the centroid of all spot detections may be calculated, to firstly establish a definite spot presence in that window, and then to relate that detected centroid position to the centroids of previous deposited spots, to check that the spacings are correct, as in FIG. 9b.

One way of doing this is to put tolerances on how far the centroids are allowed to be from their designated positions, and, possibly, to display out-of-tolerance points on the display screen of the monitor 1C in an alarm colour such as orange or red, compared to in-tolerance points in green or yellow. Biochips without spots are indicated by "X".

Figure 10:
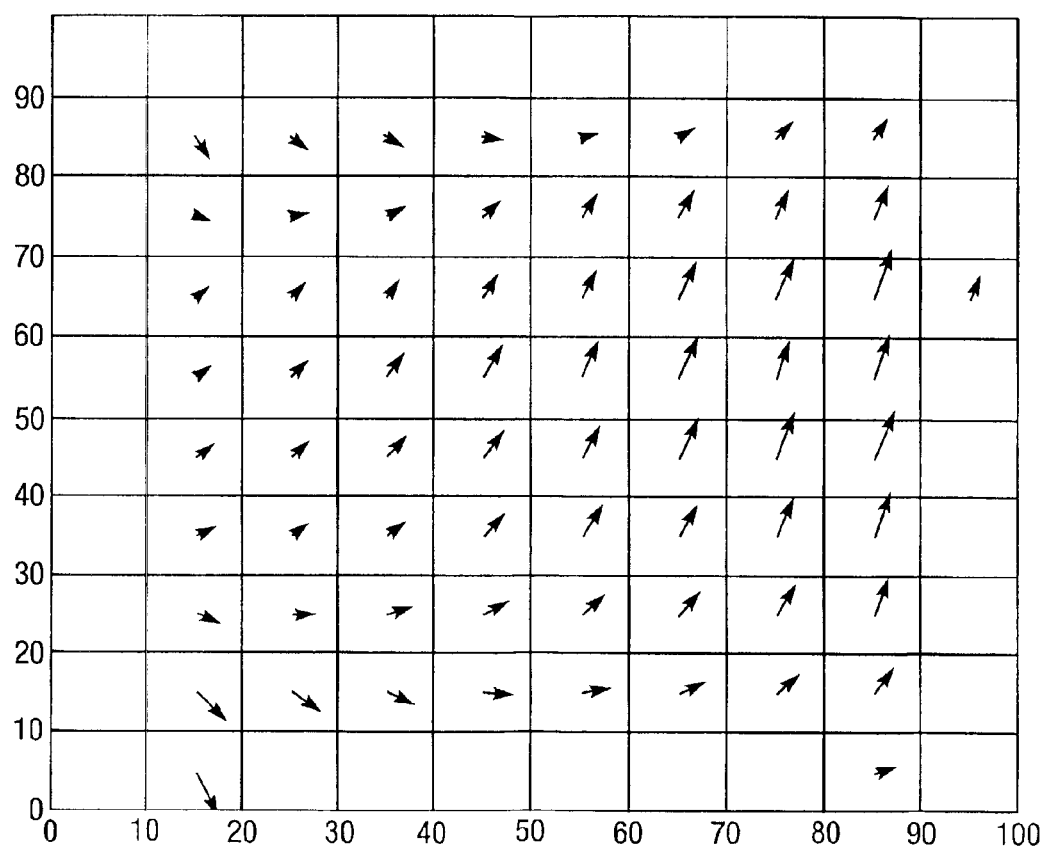
FIG. 10 illustrates positional offsets per biochip.

Calibration and spotting position offsets are typical problems faced in this type of system. The optical system can be calibrated, if required, by the standard technique of measuring a pre-defined calibration target in the camera's field of view. This might take the form of a grid of white spots on a black background, where the grid spacing matches the biochip spacing—calculation of the apparent relative spacings per grid point then gives an offset value, in both X and Y axes, that can be subtracted from each spot position to give a more accurate calculated location. This can be particularly important in the Y axis, because, without the presence of the top part of the substrate in the image, then the Y values are prone to distortion if the viewing angle is not perpendicular to the substrate. The overall problem can be made worse with lens distortion, which radially stretches or compresses the image, rendering coordinates incorrect without calibration. FIG. 10 shows typical residual offsets per biochip, after some initial correction at the top and bottom rows of the substrate.

Figure 11:
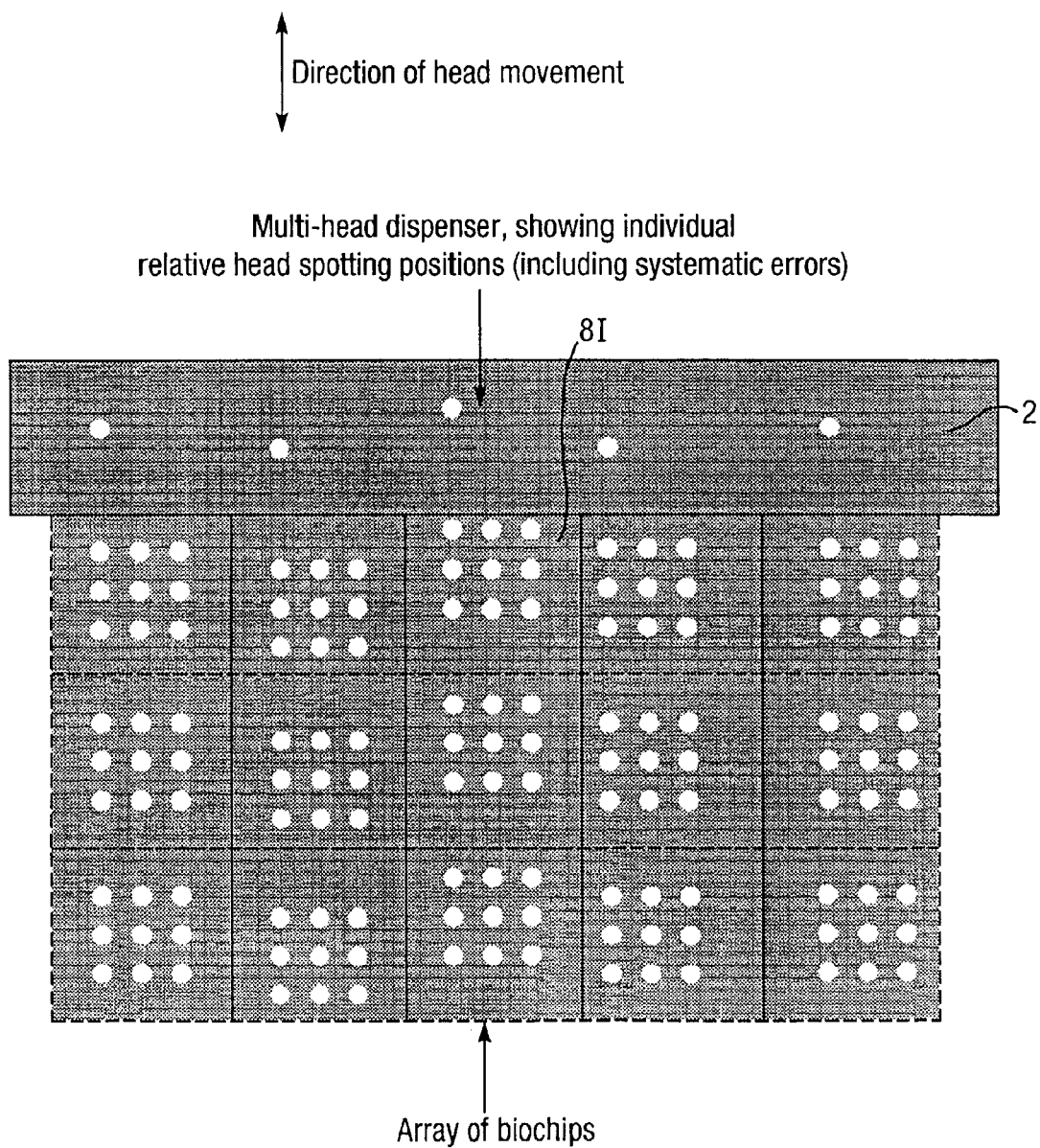
FIG. 11 illustrates spot offset errors.

Even with calibration, the multi-dispense head 2 will tend to have small offsets in the relative spot positions, along a single line of spots, because of small pointing differences between tips, and, also, minute tip shape differences, which produce a directional bias per tip. However, on a single biochip (e.g. 8I in FIG. 11), the spotting offsets will all be the same, i.e. all spots on a single biochip will be offset by the same amount, as in FIG. 11. So, as long as the average spotting offset per biochip is within acceptable limits, it does not matter if the positional processing subtracts this off set per biochip—what does matter is the relative spacings of spots within each biochip.

If it is experimentally established that the spotting offsets per biochip are within acceptable limits, then it is not strictly necessary to calibrate the vision system with a test target, since the first deposition per plate will give the relative offsets per biochip, which can then be subtracted from future spot detections, to allow relative spot gauging per biochip in real time. Of course, this and the previous techniques, require memory storage of previously detected spot centroid locations per biochip, per substrate, which may be computationally intensive. For this reason, testing of a first real-time implementation will, probably, just measure spot presence/absence per biochip, with the acceptable contrast and size variables in the machine vision program tuned to high values, so that detections of dried salts from previous spot depositions are negligible. The relative spot positions for all the spot types will be measured afterwards per substrate. The real-time processing can then be extended to the more advanced version described above.

As an adjunct to the above method, it is possible that addition of UV-fluorescent dye to the antibodies, for post-deposition detection, can be used to provide an extra safeguard against detection noise effects in the live machine vision system low angle illumination would not be necessary and frontal illumination is preferred (at nominally 90° to the surface) This would allow a separate method of checking spot position, particularly, for those biochips which the main vision program has found to be faulty. The drawback is that it may have to be implemented in a post-processing mode only, as the large number of data points per chip (since all spots are then visible at once) could render real-time positional error measurement processing too low.

Also, this method must not affect the subsequent biochip assays, and the dye would need to be washed off in the subsequent stages of chip preparation, or, if it emits at a sufficiently different wavelength from the biochip reaction, may be filtered out in the analyser using a suitable optical filter. Nevertheless, this could have the following benefits:

allows better quantification of the spot sizes, from the degree of fluorescent light output per spot, allows detection of small defects, such as satellites, that may be missed in the live system, which has to screen out noise artefacts, such as plate surface texture, allows additional confirmation of spot positions, available from a single archivable image per substrate, allows direct detection of positional errors (such as originating from plate slippage, or loss of spotting head true position from impacts thereon) that may not always be detectable in live monitoring. This is useful because, then, it is not necessary to wait until sample biochips from each substrate have been run through the analyser, to find such errors, and the result is more comprehensive, since all biochips are measured.

In another implementation, it is envisaged that the machine vision and spotting systems be fully integrated so that the vision system has direct communication with the spotter, such that the approximate spotting coordinates on the substrate are passed to the vision program. This would mean that the vision program would no longer need to use optical character recognition or barcode reading, to establish the substrate number, since this would be determinable from the spotting system coordinates.

In the embodiments described above, an OCR (Optical Character Recognition) or bar-coding is used to uniquely identify the plates. In a simpler version, such plate identification is not necessary, because the lighting, camera and vision program set-up can be arranged so that the occurrence of missed plates is extremely low—so the plates are in the correct order with a very high success rate.

One other factor which can be used to double-check the sequence of plate depositions, when post-deposition processing the data file output, is the peak in the number of detections per plate, on the last plate of each deposition sequence. This arises because the spotter 2 pauses for about one second longer at the last plate, while the heads are raised to a safe height above the biochips, and the delay allows for extra sample images to be grabbed, thus, approximately doubling the number of detections on the last plate. This confirms the position of the last plate in one deposition sequence, and the first plate of the next deposition sequence. The number of plates detected between peaks can be used to confirm that none have been missed by the detection system.

In a further alternative, a series of cameras taking close-up images of the freshly deposited spots can be provided. This could be, e.g. a series of four cameras, with a field of view of about 12 mm, horizontally, so that each camera sees two spots, the spots being on a 9 mm spacing. With 768 pixels across the image, this gives 0.015625 mm/pixel, so that a typical spot diameter of 0.6 mm covers about 38 pixels.

With this resolution, an increase of one pixel in spot diameter leads to an increase of 1.026 x, so that the change in volume would be $V1/V2=(r1/r2)^3$, where V=Volume, and r=radius, ("1" before and "2" after the increase) thus giving:

$$V1/V2 = 1.081$$

This is satisfactory for a basic measure of spot volume, although an improved measure, with the same spatial resolution, could be achieved by using the area, rather than the diameter of the detected spot. The spots would be detected by using a basic threshold technique, followed by standard "blob analysis" techniques, to segment the above-threshold pixels into discrete blobs, so that their properties (e.g. area, Y/X ratio) can be measured. The threshold level for the close-up cameras may be adjusted to much more readily find satellite spots, and jetting events, than can be achieved in the earlier embodiments where the camera covers a field of view in the region of 160×120 mm.

The Y/X ratio allows an extra measure of spot quality, as this can change progressively, if the surface condition of the spotting tip changes. This allows for an on-line diagnosis of spot quality and not just spot presence (as in the earlier embodiments), and positional accuracy. The accuracy of the area and ratio measurements can be increased by reducing the field of view of the camera heads.

Additional reliability of the above spot quality measurements can be achieved by integrating the spotter and viewing or vision system. The spotter 2 sends its X, Y position, when stationary, to the vision system so that the vision system can then send a signal to the camera(s), for image grabbing to start. This typically requires asynchronous cameras, to give a frame-on-demand output. Hence, processing will only occur for images acquired when the spotter 2 is stationary—this avoids processing motion-blurred spots, and bright artefacts around the plate edges. Also, the chip coordinates could be sent out directly to the vision system, or derived from the spotter (X, Y) position, so that the data can be correctly registered and stored against the chip indices, thus allowing for faulty chip marking on the basis of spot quality (as well as the other attributes of spot presence and position, obtained from the substrate overview camera).

As indicated above, asynchronous operation would be required, for the close up on-head cameras, to grab images, when a signal indicating the spotting state is stationary, is sent to the vision system processor 1B. This is appropriate for the scenario where an "acquire image" signal is sent from the vision program to the camera. However, as an alternative, a separate program can be written on the spotting PC or controller 2A (or indeed via an intermediate PC) using Master OLE automation, to send digital signals, when the spotter 2 is stationary, to a digital control board in a vision PC 1B. A typical vision processing package such as NeuroCheck, with digital input/output board, can then trigger the vision program to start grabbing camera images for processing, which will just happen at the next available camera field or frame, as selected, for cameras that are outputting continuous video. At the end of the desired time period, an appropriate digital signal can be sent to stop the program operating, until the next start signal is received In either case, the overall effect is to ensure that the images are grabbed only when the spotter 2 is statinary, over a chip to be examined.

We claim:

1. A method of monitoring a biochip deposit process, the method comprising:
    a) detecting spots of organic material as they are deposited on a substrate and before the spots have dried, the detecting step including illuminating the substrate at an angle which is near parallel to the plane of the substrate;
    b) determining if the spots have been correctly deposited; and,
    c) if not, generating a suitable output signal.

2. A method according to claim 1, wherein the illumination angle is in the range 0–2° with respect to the plane of the substrate.

3. A method according to claim 2, wherein the illumination angle is the range 0–1° with respect to the plane of the substrate.

4. A method according to claim 1, wherein steps b) and c) are carried out after completion of the deposit process.

5. A method according to claim 1, wherein step (a) includes obtaining an image of the spots using a camera while there is no relative movement between the camera and the substrate.

6. A method according to claim 1, wherein the output signal is generated if a spot volume lies outside a predetermined value or range.

7. A method according to claim 1, wherein the output signal is generated if the ratio between orthogonal axes of a spot lies outside a predetermined value or range.

8. A method according to claim 1, wherein the output signal is generated if a spot is not detected at an expected location.

9. A method according to claim 1, wherein the output signal is generated if a spot is offset by more than a predetermined amount from an expected location.

10. A method according to claim 8, wherein the expected location is defined with respect to other spots on the substrate.

11. A method according to claim 1, further comprising marking the or part of the substrate in response to the generation of the output signal.

12. A method according to claim 11, wherein the substrate is marked with a material which shows a detectable color, light level or densitometric change such as a colored dye, ink or wax.

13. A method according to claim 1, further comprising detecting an identifier on the substrate.

14. A method according to claim 13, wherein the detecting method is performed using an optical character or bar code reader.

15. A method according to claim 1, further comprising storing details of the detected spot locations.

16. A method according to claim 15, further comprising detecting an identifier on the substrate wherein the spot location details are stored in conjunction with the substrate identifier.

17. A method according to claim 1, wherein the detecting step comprises locating the spots; detecting a first pair of edges of the substrate; detecting the position of the located spots relative to the substrate edges; and determining if each spot is located at an expected position relative to the substrate edges.

18. A method according to claim 17, wherein the two first edges are substantially orthogonal.

19. A method according to claim 17, further comprising detecting the position of the spots relative to a second pair of substantially parallel substrate edges.

20. A method according to claim 19, wherein one of the first and second edges is common.

21. A method according to claim 1, wherein the organic material includes a fluorescent dye.

22. A method according to claim 21, further comprising detecting the spots of organic material on the substrate utilizing the fluorescent dye.

23. A method according to claim 1, wherein the substrate is opaque or translucent.

* * * * *